US007418290B2

(12) United States Patent
Devlin et al.

(10) Patent No.: US 7,418,290 B2
(45) Date of Patent: Aug. 26, 2008

(54) SYSTEM AND METHOD OF ASSESSMENT OF THE EFFICACY OF TREATMENT OF NEUROLOGICAL DISORDERS USING THE ELECTROENCEPHALOGRAM

(75) Inventors: Philip H. Devlin, Brookline, MA (US); Scott D. Greenwald, Norfolk, MA (US)

(73) Assignee: Aspect Medical Systems, Inc., Norwood, MA (US)

( * ) Notice: Subject to any disclaimer, the term of this patent is extended or adjusted under 35 U.S.C. 154(b) by 296 days.

(21) Appl. No.: 10/840,343

(22) Filed: May 6, 2004

(65) Prior Publication Data

US 2005/0043774 A1 Feb. 24, 2005

Related U.S. Application Data

(60) Provisional application No. 60/468,350, filed on May 6, 2003, provisional application No. 60/534,247, filed on Jan. 5, 2004.

(51) Int. Cl.
*A61B 5/04* (2006.01)
(52) U.S. Cl. ...................... 600/544; 600/545
(58) Field of Classification Search .............. 600/544, 600/545, 300, 301
See application file for complete search history.

(56) References Cited

U.S. PATENT DOCUMENTS 4,907,597 A 3/1990 Chamoun
5,010,891 A 4/1991 Chamoun
5,269,315 A 12/1993 Leuchter et al.
5,299,569 A 4/1994 Wernicke et al.
5,309,923 A 5/1994 Leuchter et al.
5,320,109 A * 6/1994 Chamoun et al. ............ 600/544
5,458,117 A 10/1995 Chamoun et al.
5,871,517 A * 2/1999 Abrams et al. ................ 607/45
6,066,163 A * 5/2000 John ............................ 607/45
6,205,359 B1 * 3/2001 Boveja ........................ 607/45
6,263,237 B1 7/2001 Rise
6,425,852 B1 * 7/2002 Epstein et al. ................ 600/13
6,459,936 B2 10/2002 Fischell et al.
6,463,328 B1 10/2002 John
6,539,263 B1 3/2003 Schiff et al.
6,622,036 B1 9/2003 Suffin (Continued)

OTHER PUBLICATIONS

U.S. Appl. No. 60/468,350, filed May 6, 2003, Devlin et al.

(Continued)

*Primary Examiner*—Robert L. Nasser, Jr.
*Assistant Examiner*—Karen E Toth
(74) *Attorney, Agent, or Firm*—Wilmer Curtis Pickering Hale & Dorr LLP.

(57) ABSTRACT

Disclosed is a system and method of assessing the efficacy of treatment of neurological or psychological disorders. The preferred embodiment uses at least two surface electrodes to acquire EEG signals from the surface of a patient's body, a processor for computing from the EEG signals various features and indices that are representative of the patient's neurological or psychological state. Changes in these parameters may be used to assess the efficacy of treatment and to modify the treatment to optimize the resultant patient state.

38 Claims, 3 Drawing Sheets

U.S. PATENT DOCUMENTS

| | | | |
|---|---|---|---|
| 2002/0013612 | A1 | 1/2002 | Whitehurst |
| 2003/0023282 | A1* | 1/2003 | Barrett et al. .................. 607/45 |
| 2003/0181821 | A1* | 9/2003 | Greenwald et al. .......... 600/544 |
| 2003/0204135 | A1* | 10/2003 | Bystritsky ................... 600/407 |
| 2005/0216071 | A1 | 9/2005 | Devlin et al. |

OTHER PUBLICATIONS

U.S. Appl. No. 60/534,247, filed Jan. 5, 2004, Devlin et al.

Jasper, J., "The Ten Twenty Electrode System of the International Federation," Electroencephalography and Clinical Neurology, (1958) The EEG Journal, vol. 10, pp. 371-375.

Alkire, M. T., "Quantitative EEG Correlations with Brain Glucose Metabolic Rate During Anesthesia in Volunteers," Anesthesiology, 1998, vol. 89(2), pp. 323-333.

Jasper, H. H., "The Ten-Twenty Electrode System of the International Federation in Electroencephalography and Clinical Neurology," The EEG Journal, 1958, vol. 10 (Appendix), pp. 371-375.

Murphy, J. V. et al., "Stimulation of the Nervous System for the Management of Seizures," CNS Drugs, 2003, vol. 17(2), pp. 101-115.

Rampil, I. J., "A Primer for EEG Signal Processing in Anesthesia," Anesthesiology, 1998, vol. 89(4), pp. 980-1002.

* cited by examiner

SYSTEM AND METHOD OF ASSESSMENT OF THE EFFICACY OF TREATMENT OF NEUROLOGICAL DISORDERS USING THE ELECTROENCEPHALOGRAM

CROSS REFERENCE TO RELATED APPLICATIONS

This application claims priority to U.S. Provisional Application Ser. No. 60/468,350 filed on May 6, 2003 and U.S. Provisional Application Ser. No. 60/534,247 filed on Jan. 5, 2004.

BACKGROUND OF THE INVENTION

There are a wide range of neurological and psychological disorders for which treatment may be provided by various means. For many disorders, administration of pharmaceutical agents is the most common treatment modality. In cases in which the symptoms of the disorder are resistant to pharmacological treatment or for which no pharmacological treatment exists, other modalities may be used, including neurostimulation.

Neurostimulation is a method of disease treatment which uses an electrical stimulator to provide a current signal which is used to stimulate the central nervous system (CNS), generally either directly or by means of a nerve of the peripheral nervous system. Such neurostimulators and their corresponding electrodes are generally implanted in a patient's body. There are currently two primary methods of neurostimulation for central nervous system disorders; deep brain stimulation (DBS) and vagus nerve stimulation (VNS). DBS uses an electrode implanted directly in a patient's brain, while VNS stimulates a patient's vagus nerve peripherally.

A commercially available DBS neurostimulator is manufactured and sold by Medtronic Inc. of Minneapolis, Minn., USA, model 3386, having a stimulating lead with four cylindrical stimulating electrodes. The deep brain stimulator is a surgically implanted medical device, similar to a cardiac pacemaker, which delivers high-frequency, pulsatile electrical stimulation to precisely targeted areas within the brain. The device consists of a very small electrode array (electrodes 1.5 mm in length with 3 mm center to center separation) placed in a deep brain structure and connected through an extension wire to an electrical pulse generator surgically implanted under the skin near the collarbone. The Medtronic DBS has received marketing clearance from the US Food and Drug Administration (FDA) with an indication for treatment of Parkinson's Disease, Essential Tremor, and Dystonia. Current research is evaluating DBS as a treatment for epilepsy, psychiatric disorders, and chronic pain.

The DBS stimulator is surgically placed under the skin of the chest of the patient. The stimulating DBS electrode lead is connected to the DBS stimulator wires and is placed in a specific inter-cranial location which may vary depending on the region of the brain being treated. The DBS system is adjusted by several parameters: 1. location of the 4 electrode lead, 2. selection of the stimulating electrodes, 3. amplitude of the stimulator signal, 4. frequency (repetition rate) of the stimulator signal, 5. polarity of the stimulating signal, and 6. pulse width of the stimulating signal. Post-implantation, all of these parameters except electrode location can be non-invasively varied by a clinician to enhance therapeutic effectiveness and minimize side effects. Amplitude, measured in volts, is the intensity or strength of the stimulation. The typical range is 1.5 to 9 volts. Frequency is the repetition rate at which the stimulation pulse is delivered and is measured in pulses per second (Hz); it typically ranges from 100-185 Hz. The pulse width is the duration of the stimulation pulse, measured in microseconds. The average pulse width ranges from 60-120 microseconds.

Another commercially available neurostimulator is designed for use on the peripheral nervous system, specifically the vagus nerve. An example of this type of system is designed and sold by Cyberonics Corporation. The Vagus Nerve Stimulator (VNS) Therapy device is implanted in a patient's chest under the skin immediately below the collarbone or close to the armpit. Two tiny wires from the device wrap around the vagus nerve on the left side of the neck. Through stimulation of this peripheral nerve, brain function is affected. VNS therapy has been granted marketing clearance by the FDA with an indication for treatment of epilepsy and is being investigated to treat a number of other central nervous system diseases and conditions, such as depression, obesity, Alzheimer's disease, etc.

An obstacle to the broader use of these devices is, in many indications, the lack of a measure of treatment efficacy. The efficacy of neurostimulation is a function of the settings of the various stimulator parameters (i.e., electrode selection, stimulus pulse amplitude, stimulus pulse frequency, stimulus polarity and stimulus pulse width, among others). However, with the exception of treatment for essential tremor or patients with very frequent epileptic seizures, it is difficult to assess the effect of the stimulus provided, and thus difficult to adjust these parameters to achieve the maximum possible treatment efficacy.

Prior Art

A number of different approaches have used the EEG as a feedback signal for neurostimulation.

In U.S. Pat. No. 6,263,237 issued to Rise, the use of a sensor in combination with a signal generator (neurostimulator) to treat an anxiety disorder is described. In this embodiment, the sensor generates a signal related to a condition resulting from the anxiety disorder. Control means responsive to the sensor signal regulate the signal generator so that the neurological disorder is treated. One of the types of sensor signals is cortical potentials recorded above the neurons controlling specific aspects of behavior associated with the neurological disorder; in this case, the sensor would take the form of an implanted depth electrode. In this system, the sensor is an integral component of the stimulating device. There is no teaching or suggestion in the patent, however, of the method of obtaining or computing a sensor signal relating to the anxiety disorder or to treatment efficacy.

In U.S. Pat. No. 6,066,163 issued to John, an Adaptive Brain Stimulation (ABS) system which aids in the rehabilitation of patients from traumatic brain injury, coma, or other brain dysfunction is described. The system comprises a sensor(s), a stimulating means, a comparator means for statistical comparison, and a means to adjust the stimulator according to the outcome of the comparison. The object of the system is to improve treatment of central nervous system pathology such as coma by relying on statistically significant and medically meaningful criteria to choose a specified program of stimulation. The John system specifically utilizes signals from the brain (EP and EEG), as well as EKG and EMG. John describes a large number of potential parameters that may be computed from these signals. The parameters are compared using statistical methods to a set of reference values from a database which may include values previously obtained from the patient, values that medical personnel have obtained, or values from an appropriate normative population. The ABS then selects a set of stimulation parameters based upon this comparison. A positive outcome is defined as the current state meeting a set of criteria indicating an improvement in the patient's condition. John describes the method only in a general sense; the patent does not teach any specific method or the use of any specific signals or parameters to quantify those signals, nor does it teach criteria which define positive outcomes. In addition, John does not teach the making of an index of treatment efficacy.

U.S. Pat. No. 6,539,263 issued to Schiff et al. describes a system for treating a conscious patient to improve cognitive function or coordination of function across a patient's cortical regions. Electrical stimulation is applied to at least a portion of the subcortical structures involved in the generation and control of generalized efference copy signals under conditions effective to improve the patient's cognitive function. Internally generated movement of the patient is then detected and in response to such internally generated movement, application of electrical stimulation is controlled. Schiff, et al. also state that their method can be optimized by monitoring regional and intrahemispheric changes in brain waves as measured by conventional techniques (EEG or magnetoencephalogram (MEG)) or by monitoring regional and intrahemispheric changes in metabolic activity. Schiff, et al., however, do not teach specific methods for processing the EEG or MEG signal to produce a parameter reflective of cognitive function.

U.S. Published Patent Application 2002/0013612A, filed by Whitehurst, describes a system for applying drugs and/or applying electrical stimulation to the brain to treat mood and/or anxiety disorders. The system described is fully implanted in the skull. In order to help determine the strength and/or duration of electrical stimulation and/or the amount and/or type(s) of stimulating drug(s) required to produce the desired effect, in one preferred embodiment, a patient's response to and/or need for treatment is sensed. Whitehurst states that the methods of determining the required electrical and/or drug stimulation include measuring the electrical activity of a neural population (e.g., EEG), measuring neurotransmitter levels and/or their associated breakdown product levels, measuring medication and/or other drug levels, hormone levels, and/or levels of any other bloodborne substance(s). He further states that the sensed information is preferably used to control the stimulation parameters of the System Control Unit(s) in a closed-loop manner. Whitehurst does not teach any method of processing the EEG signal to produce a parameter that can be used as a control variable, nor does he teach recording EEG from the surface of the head.

Others have examined EEG asymmetries (i.e., differences EEG metrics between brain hemispheres); "The common observation in electroencephalographic (EEG) studies of an altered pattern of asymmetric activation in anterior scalp regions in the reduced left relative to right activation in depressed or dysphoric individuals . . . ".

A principal object of the present invention is to derive clinically meaningful information from the electroencephalogram signal to help optimize neurostimulation therapy.

SUMMARY OF THE INVENTION

The present invention describes a system and method for assessing the efficacy of treatment for neurological or psychological conditions. Treatment efficacy is assessed by interpretation of changes in the EEG signal. It is well known that neurostimulation of the thalamus can influence the EEG. This invention is based on the concept that excitation or inhibition of brain circuits is manifested in specific EEG changes that can be characterized by and associated with the efficacy of Deep Brain Stimulation or Vagus Nerve Stimulation treatment.

The invention described in this application enables the quantification and monitoring of the efficacy of various methods of treatment of neurological and psychological disorders. In the preferred embodiment the efficacy of neurostimulation of the peripheral and/or central nervous system is quantified. Examples of diseases and conditions to which the invention may be applied include depression, obsessive compulsive disorder, epilepsy, Parkinson's disease, movement disorders, and stroke. Similarly, while the preferred embodiment describes the quantification of the efficacy of neurostimulation, this invention may be used to monitor the efficacy of other types of treatment as well, including but not restricted to pharmacological treatment, electroconvulsive therapy (ECT) and transcranial magnetic simulation (TMS).

In the case of inhibition of brain function via deep brain or vagus nerve stimulation, a disruption of a cortex to deep-brain neuro-transmission signal path may occur. This would result in a decrease in EEG signal power. Conversely, if the neurostimulation activates or enhances a neuro-transmission pathway, an increase in EEG signal power may occur. Observations of DBS patients indicate that the neurostimulation used currently to treat patients suffering from obsessive-compulsive disorder and depression by bilaterally stimulating the anterior limb of the internal capsule (an anatomical region of the brain near the thalamus) causes a reduction in frontal EEG power referenced to the left earlobe and the right earlobe, specifically in the alpha (8-12 Hz) and/or theta (4-8 Hz) frequency bands. This decrease in power is consistent with the hypothesis that frontal alpha power is generated by a cortex-to-thalamus neuro-pathway and that the DBS interferes with that pathway.

The invention described herein processes the EEG signals that are directly or indirectly affected by the area of the brain that is being stimulated. An index of neurostimulation treatment efficacy is generated from the EEG signal using spectral and/or time-domain features. A skilled clinician then adjusts the neurostimulator settings or location based on the EEG changes. The preferred embodiment uses EEG measured from two EEG channels, left earlobe ($A_1$) referenced to the forehead midline ($Fp_Z$) and right earlobe ($A_2$) referenced to $Fp_Z$ in combination. The two EEG signals are then used to calculate a numerical index which is reflective of the efficacy of neurostimulator treatment. This methodology can be extended to apply to other EEG parameters (including those that are time-based as well as frequency-based) obtained from other electrode locations and other modes of treatment of the brain including both device and pharmacological treatments.

These and other features and objects of the present invention will be more fully understood from the following detailed description which should be read in light of the accompanying drawings in which corresponding reference numerals refer to corresponding parts throughout the several views.

DETAILED DESCRIPTION OF THE PREFERRED EMBODIMENT

Figure 1:
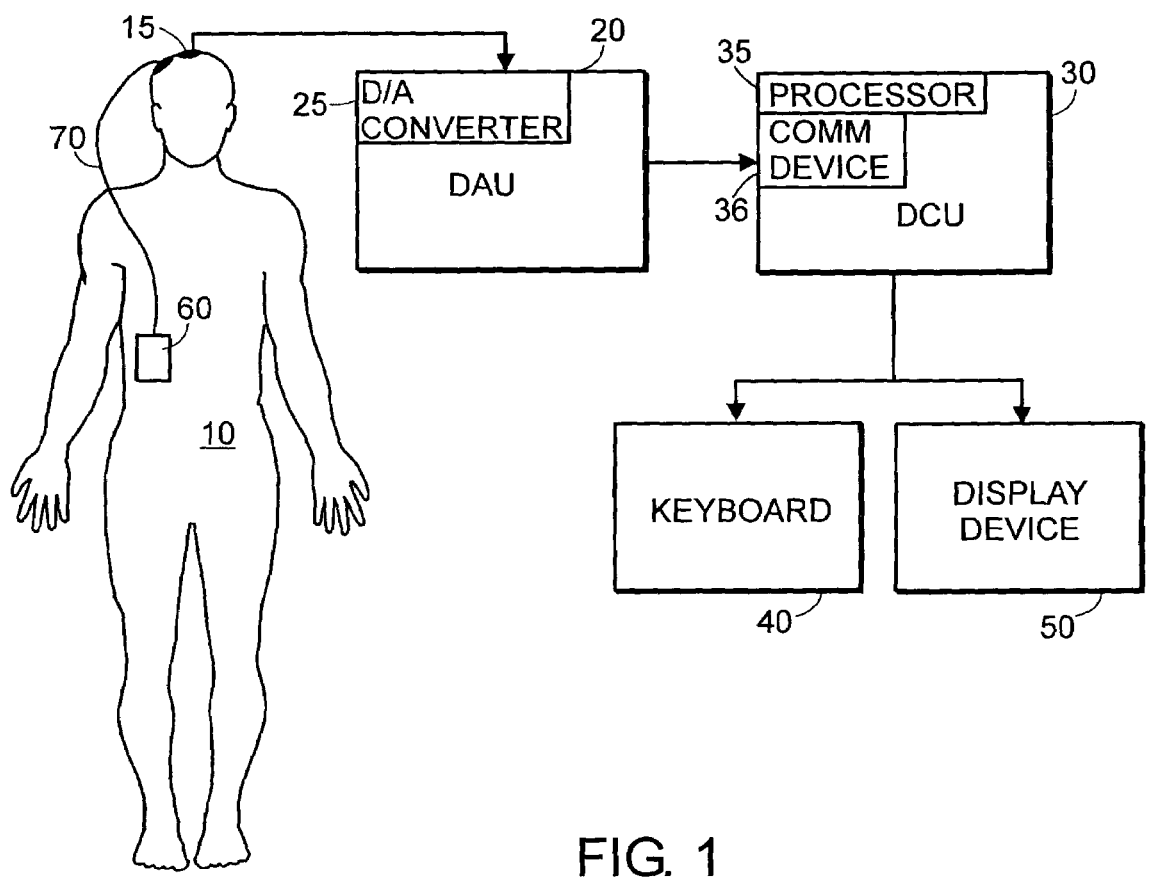
FIG. 1 is a block diagram of the system of the present invention.

The invention described herein is a method of assessing the efficacy of treatment of neurological and psychiatric disorders by assessing changes in neuronal activity as manifested in the EEG. A particular embodiment of the invention involves a system for assessing the effect of the electrical stimulation provided by a neurostimulator 60 connected to a patient 10 via a stimulating electrode lead 70 (FIG. 1). The system incorporates a Data Acquisition Unit (DAU) 20 used to acquire a subject's EEG signal for subsequent processing. The DAU 20 typically consists of a computer system with an integral analog-to-digital (A-D) converter 25 and a set of electrodes 15 that are placed on the scalp of a subject 10. The A-D converter is used to transform analog EEG signals obtained from a set of surface electrodes into a sampled set of signal values that may then be analyzed by the computer of the Data Computation Unit (DCU) 30. The DCU 30 incorporates a processor 35 and a communications device 36 that receives the sampled values from the DAU 20. In this embodiment, the processors of the DAU 20 and DCU 30 are one and the same. In alternate embodiments, however, the DAU 20 may acquire the EEG signals and transmit the sampled EEG signals over a communications link to a remote DCU 30. Such a communications link may be a serial or parallel data line, a local or wide area network, a telephone line, the Internet, or a wireless connection. The clinician conducting the assessment may communicate with the DCU 30 using a keyboard 40 and display device 50.

EEG data is acquired from the surface of a patient's body using surface electrodes 15. When the electrodes are all to be placed below the hairline, the electrodes are preferably of the Zipprep® type manufactured by Aspect Medical Systems, Inc. (Newton, Mass.). When electrodes are placed within the hair, gold-cup type electrodes may be used, held in place by either collodion or a physical restraint. A variety of different electrode placements, or montages, may be used. The preferred embodiment uses an electrode arrangement (montage) of the left earlobe ($A_1$) referenced to the center of the forehead ($Fp_z$) and the right earlobe ($A_2$) referenced to $Fp_z$ in combination, in which a first channel of EEG signal is the voltage observed between electrode locations $A_1$ and $Fp_z$ ($A_1$-$Fp_z$) and a second channel of EEG is the voltage observed between electrode locations $A_2$ and $Fp_z$ ($A_2$-$Fp_z$). An alternate embodiment uses an electrode montage in which the first channel is the voltage between electrode locations $F_7$-$Fp_z$ and a second channel of EEG is the voltage observed between electrode locations $F_8$-$Fp_z$. Another alternate embodiment uses the BIS Sensor (Aspect Medical Systems Inc.), which uses the unilateral montage of $Fp_z$-At1, $Fp_z$-$SM94_1$, where At1 is on the left temple lateral to the eye (0.75 inches anterior to the malar bone) and $SM94_1$ is 2.5 inches lateral to $Fp_z$. This montage is described as being on the left side of the head, but may equivalently be on the right side, in which case it is denoted as $Fp_z$-At2, $Fp_z$-$SM94_2$. Alternatively, any configuration of electrode locations may be used, such as those described by the International 10/20 Electrode Montage System described by HH Jasper in "The Ten-Twenty Electrode System of the International Federation in Electroencephalography and Clinical Neurology", The EEG Journal, 1958; 10 (Appendix), pp. 371-5., using both referential and unipolar configurations.

EEG signals acquired by the electrodes 15 are sampled by the D/A converter 25 of the DAU 20 to create a sampled data set, preferably at a sampling rate of 128 samples/second. The sampled data set is divided for analysis purposes in the preferred embodiment into 2 second (256 sample) records (epochs). After the DCU 30 receives the sampled values from the DAU 20, the DCU 30 first examines the sampled EEG signals for artifact arising from patient movement, eye blinks, electrical noise, etc. Detected artifact is either removed from the signal, or the portion of the signal with artifact is excluded from further processing. High-pass filtering is also employed to reduce the tendency of power at frequencies above the signal band of interest from appearing at lower frequencies due to an inadequate sampling frequency (aliasing).

The DCU 30 next computes a set of parameters from the artifact-free EEG data. Such parameters may include power spectral arrays, bispectral arrays, higher-order spectral arrays (trispectrum, etc.), cordance (such as described in U.S. Pat. Nos. 5,269,315 and 5,309,923), z-transformed variables, entropy parameters, and time-domain parameters, including but not limited to template matching, peak detection, threshold crossing, zero crossings and Hjorth descriptors. Such parameters, spectral or otherwise, which quantify some aspect of the data are referred to as features. The DCU 30 calculates from the parameters a series of features and indices that are indicative of the subject's severity of neurological dysfunction or level of neurological condition. By observing how these features and indices change in response to the neurostimulation provided by the neurostimulator 60, the stimulation parameters may be varied to modulate the neurostimulation effect. These features and indices may be displayed to the user on the display device 50. In the embodiment in which the DCU 30 is remote from the DAU 20, the result may be transmitted back to a display device on the DAU 20, or transmitted to the patient's physician via e-mail or made available via a secure web page.

Calculation of the Spectral Arrays

In the preferred embodiment, the features of the index are calculated from spectral arrays, defined as any of the power spectral arrays, bispectral arrays or higher-order spectral arrays (trispectrum, etc.), The power spectral and bispectral data arrays may be calculated using frequency domain (Fourier transform) methods as well as time domain (autoregressive) methods. The term power spectral arrays or power spectrum includes any or all of the power spectral, cross spectral and coherence arrays. The term bispectral arrays or bispectrum includes all or any of the following arrays, for both auto and cross formulations: complex triple product, real triple product, bispectral density, biphase and bicoherence arrays. The power spectral arrays are calculated as an intermediate step of the bispectral array computation and are thus available for the derivation of parameters to be used as features in an index. In the case in which only power spectral arrays are used to calculate an index, the computation may be ended after the needed arrays are computed. Both frequency and time domain methods will be illustrated here, and those skilled in the art will recognize that other methods may potentially be derived, as well. The invention is intended to incorporate all computational methods of obtaining the power spectral and bispectral arrays.

Figure 2:
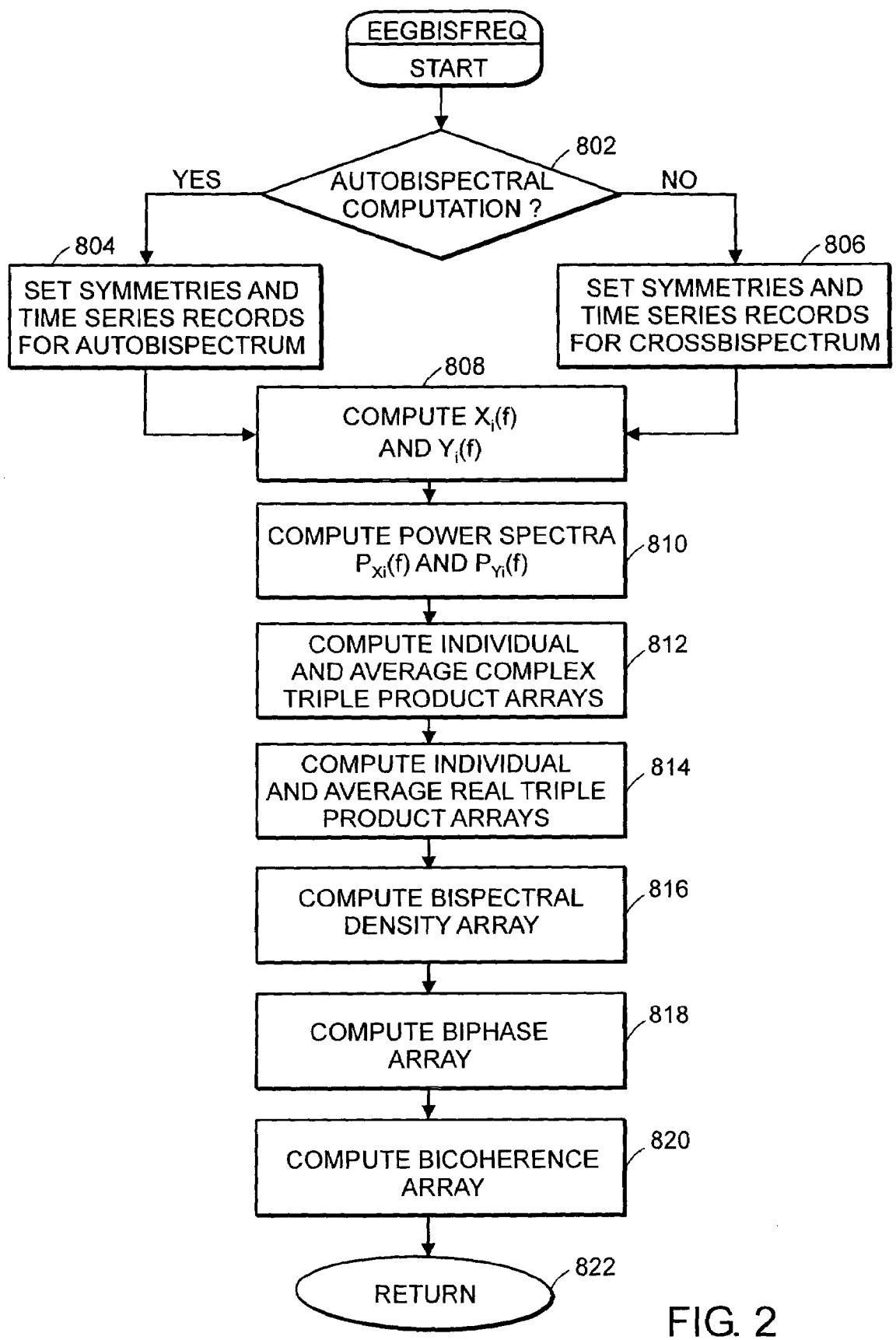
FIG. 2 is a flow chart of a method of computation of the power spectral and auto/cross bispectral arrays of the present invention.

Referring now to FIG. 2, the frequency domain-based procedures for producing the power spectral, cross-spectral, coherence, autobispectral or the cross-bispectral arrays will now be discussed. In step 802, the system checks whether the computation to be performed is an autospectral or cross-spectral computation. Autobispectral analysis is a special case of cross-bispectral analysis and therefore different rules of symmetry apply.

In step 804, the system sets the following symmetries in order to proceed with autobispectral computation:

$$f_1 + f_2 \leq f_s/2$$

$$0 \leq f_2 \leq f_1$$

where $f_s$ is the sampling rate (128 samples/second in the preferred embodiment which uses 128 2-second records, resulting in a frequency resolution of 0.5 Hz), and $f_1$ and $f_2$ (also referred to as Frequency 1 and Frequency 2) denote the frequency pairs over which cross-spectral or bispectral computation will be carried out. In addition, for the power spectral and autobispectral computation, $$X_i(t) = Y_i(t) \rightarrow X_i(f) = Y_i(f)$$

$X_i(t)$ and $Y_i(t)$ denote the individual time series records used for power and bispectral computation. In the preferred embodiment, $X_i(t)$ and $Y_i(t)$ are sampled EEG records obtained simultaneously from different channels. They may also be successive records from the same channel. $X_i(f)$ and $Y_i(f)$ denote the Fourier transforms of the time series records $X_i(t)$ and $Y_i(t)$, respectively, and i denotes the record number.

In step 806, the following symmetries are adhered to for cross-bispectral analysis:

$$f_1 + f_2 \leq f_s/2$$

$$0 \leq f_1 \leq f_s/2$$

$$0 \leq f_2 \leq f_s/2$$

$$X_i(t) \neq Y_i(t) \rightarrow X_i(f) \neq Y_i(f)$$

where all variables represent the same values as they do for autobispectral analysis, except that for cross-spectral analysis $X_i(t)$ and $Y_i(t)$ represent individually derived time series records.

The fast Fourier transform (FFT) $X_i(f)$ and $Y_i(f)$ of the selected records is computed using a standard IEEE library routine or any other publicly available routine in step 808.

In Step 810, the power spectra $P_{Xi}(f)$ and $P_{Yi}(f)$ of each of the selected records is computed by squaring the magnitudes of each element of the Fourier transforms $X_i(f)$ and $Y_i(f)$, respectively.

$$P_{Xi}(f) = |X_i(f)|^2$$

$$P_{Yi}(f) = |Y_i(f)|^2$$

The cross spectral array $P_{XY}(f)$ and the coherence array $\gamma_{XY}^2(f)$ may also be calculated as:

$$P_{XY_i}(f) = X_i^*(f) Y_i(f)$$

$$P_{XY}(f) = \frac{1}{M} \sum_{i=1}^{M} P_{XY_i}(f)$$

$$P_X(f) = \frac{1}{M} \sum_{i=1}^{M} P_{X_i}(f)$$

$$P_Y(f) = \frac{1}{M} \sum_{i=1}^{M} P_{Y_i}(f)$$

$$\gamma_{XY}^2(f) = \frac{|P_{XY}(f)|^2}{P_X(f) P_y(f)}$$

where $X_i^*(f)$ is the complex conjugate of $X_i(f)$ and M is the number of records (128 in the preferred embodiment).

The system computes the average complex triple product in step 812 by utilizing the following equations where $bc_i(f_1, f_2)$ is the individual complex triple product from one record and $BC(f_1, f_2)$ is the average complex triple product:

$$bc_i(f_1, f_2) = X_i(f_1) Y_i(f_2) Y_i^*(f_1 + f_2)$$

where $Y_i^*(f_1 + f_2)$ is the complex conjugate of $Y_i(f_1 + f_2)$, and $$BC(f_1, f_2) = \frac{1}{M} \sum_{i=1}^{M} bc_i(f_1, f_2)$$

The average real triple product is computed in step 814 by using the following equations where $P_{Xi}(f)$ and $P_{Yi}(f)$ are the power spectra from one record, $br_i(f_1, f_2)$ is an individual real triple product from one record and $BR(f_1, f_2)$ is the average real triple product:

$$br_i(f_1, f_2) = P_{Xi}(f_1) P_{Yi}(f_2) P_{Yi}(f_1 + f_2)$$

$$BR(f_1, f_2) = \frac{1}{M} \sum_{i=1}^{M} br_i(f_1, f_2)$$

Note that $P_{Yi}$ is real valued, and therefore $P_{Yi} = P_{Yi}^*$.

In step 816, the bispectral density array $BD(f_1, f_2)$ is computed using the following equation:

$$BD(f_1, f_2) = |BC(f_1, f_2)|$$

In step 818, the system computes the biphase array $\phi(f_1, f_2)$ using the following equation:

$$\phi(f_1, f_2) = \tan^{-1}\left(\frac{\text{Im}(BC(f_1, f_2))}{\text{Re}(BC(f_1, f_2))}\right)$$

$$0 \leq \phi \leq 2\pi \text{ (radians)}$$

In step 820, the system computes the bicoherence array $R(f_1, f_2)$ using the following equation:

$$R(f_1, f_2) = \frac{BD(f_1, f_2)}{\sqrt{BR(f_1, f_2)}}$$

$$0 \leq R \leq 1$$

In step 822, the system returns the requested auto/cross bispectral arrays to the Data Computation Unit 30.

Figure 3:
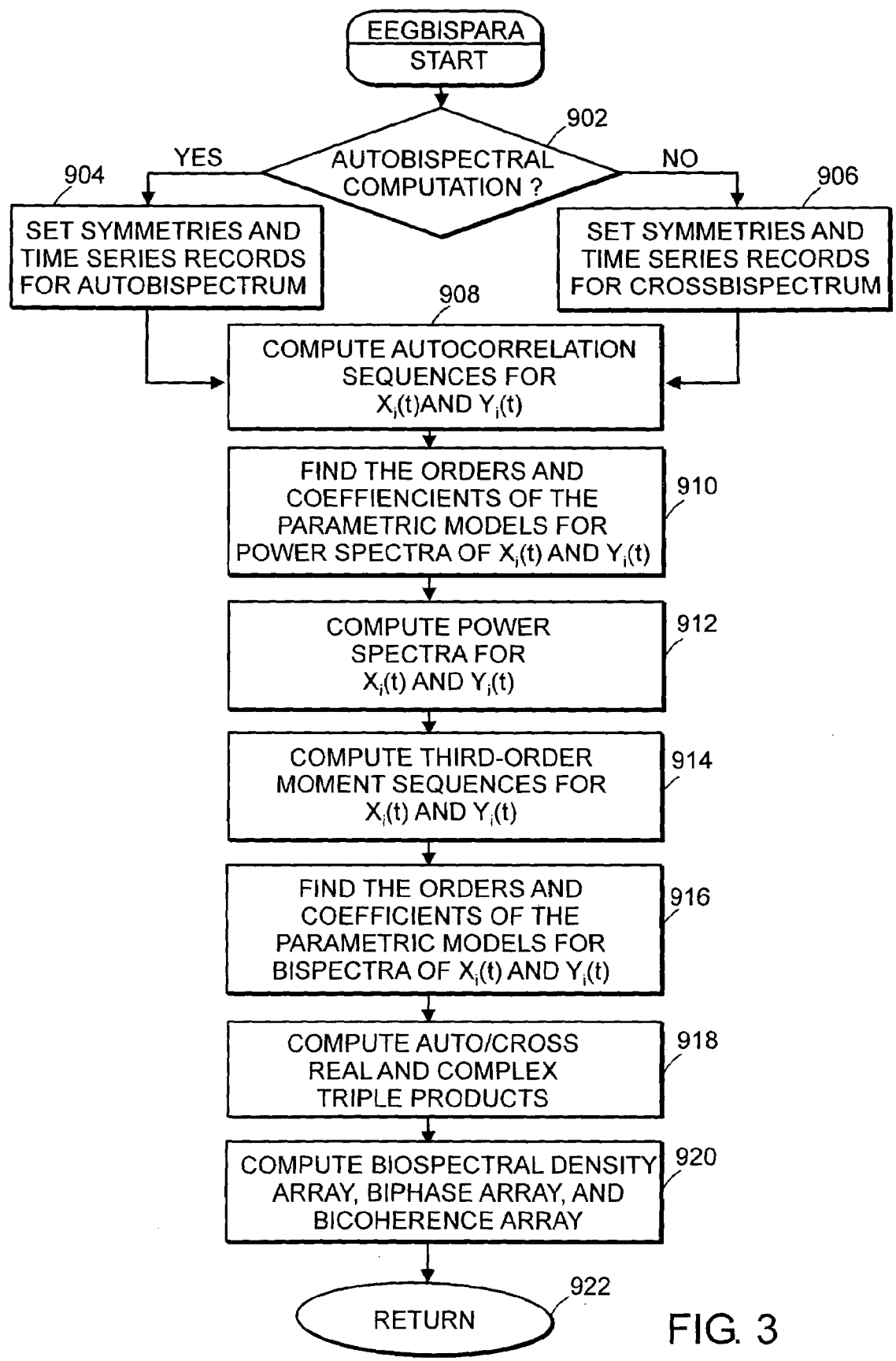
FIG. 3 is a flow chart of an alternate method of computation of the power spectral and auto/cross bispectral arrays of the present invention.

Now turning to FIG. 3, a parametric based method for calculating the auto/cross bispectral arrays will now be described. In steps 902, 904, and 906 the system sets the symmetries and time series records in the same manner as described above in steps 802, 804, and 806 respectively. The power spectra of $X_i(t)$ and $Y_i(t)$ are estimated in steps 908, 910, and 912. In addition, the cross spectral and coherence arrays are computed. This estimation method includes two major stages, the autoregressive (AR) model order selection and the power spectrum computation for $X_i(t)$ and $Y_i(t)$. In step 908, the system computes two sequences of autocorrelations, $\{R_{2X}(m)\}$ and $\{R_{2Y}(m)\}$ using the following equation.

$$R_{2z}(m) = \frac{1}{M*N} \sum_{i=1}^{M} \sum_{t=0}^{N-|m|} z_i(t) z_i(t+m)$$

$z = X, Y,$ and $m = 0, 1, \ldots, L$ where M is the number of records and N is the number of samples per record (128 and 256, respectively, in the preferred embodiment), and L is much greater than the possible AR filter order (L=50 in the preferred embodiment). The Final Prediction Errors, $FPE_X(m)$ and $FPE_Y(m)$ are calculated for all orders, m=0, 1, 2, . . . L, by performing a Levinson recursion function on each autocorrelation sequence in step 910 in order to find the order of the AR filter. The locations of the minima of $FPE_X(m)$ and $FPE_Y(m)$, $Q_X$ and $Q_Y$, respectively, are chosen to be the orders of the AR filters of power spectra of $X_i(t)$ and $Y_i(t)$ respectively, i.e., $FPE_X(Q_X) = \min\{FPE_X(m)\}$ $FPE_Y(Q_Y) = \min\{FPE_Y(m)\}$ Once the orders of the AR filters for power spectra are chosen, the autocorrelation sequences, $\{R_{2X}(m)\}$ and $\{R_{2Y}(m)\}$, are entered into Levinson recursion with orders $Q_X$ and $Q_Y$, respectively, instead of L. The coefficients, $\{c_{iX}, i=0, 1, \ldots, Q_X\}$ and $\{c_{iY}, i=0, 1, \ldots, Q_Y\}$, obtained from the recursion are the coefficients of the AR filters for the power spectra of $X_i(t)$ and $Y_i(t)$, respectively. Then, in step 912, the power spectra $P_X(f)$ and $P_Y(f)$ are computed as the prediction error ($\sigma_z^2$) divided by square of the magnitude of the Fourier transform of the coefficients, i.e., $$P_z(f) = \frac{\sigma_z^2}{\left|1 + \sum_{i=1}^{Q_z} c_{iz} e^{-j2\pi f i}\right|^2}$$

$z = X, Y$

Similarly, the cross spectra $P_{xy}(f)$ can be calculated as $$P_{XY}(f) = \frac{\sigma_X \sigma_Y}{\left|1 + \sum_{i=1}^{Q_X} c_{iX} e^{-j2\pi f i}\right| \left|1 + \sum_{i=1}^{Q_Y} c_{iY} e^{-j2\pi f i}\right|}$$

and the coherence array is calculated from $P_x(f)$, $P_y(f)$ and $P_{xy}(f)$ as above.

The system estimates the auto/cross real and complex triple products in steps 914, 916, and 918. The estimation process includes two major stages: the order selection and real and complex triple product computation. In step 914, two sequences of third-order moments, $\{R_{3X}(\tau)\}$ and $\{R_{3Y}(\tau)\}$ are computed using the following equation.

$$R_{3z}(\tau) = \frac{1}{M*N} \sum_{i=1}^{M} \sum_{t=s_1}^{s_2} z_i(t) z_i^2(t+\tau)$$

$z = X, Y,$ and $\tau = -L, \ldots, L$ where $s_1 = \max(1, 1-\tau)$, $s_2 = \min(N, N-\tau)$, and L is much greater than the possible AR filter orders (e.g. 50).

In step 916, two super matrices $T_X$ and $T_Y$ are formed as follows.

$$T_z = \begin{pmatrix} R_{3z}(-L) & R_{3z}(-L+1) & \cdots & R_{3z}(0) \\ R_{3z}(-L-1) & R_{3z}(-L) & \cdots & R_{3z}(-1) \\ \vdots & \vdots & \vdots & \vdots \\ R_{3z}(-2L) & R_{3z}(-2L+1) & \cdots & R_{3z}(-L) \end{pmatrix}$$

$z = X, Y$

From the assumption we made about the AR filter of the bispectral arrays, the orders $O_X$ and $O_Y$ of the AR filters of the bispectral arrays of $X_i(t)$ and $Y_i(t)$ are the ranks of the super matrices $T_X$ and $T_Y$. Therefore, $O_X$ and $O_Y$ are chosen by using singular value decomposition. Having found the orders, we obtain the coefficients of the AR filters of the bispectral arrays by solving the following linear system of equations:

$$\begin{pmatrix} R_{3z}(0) & R_{3z}(1) & \cdots & R_{3z}(O_z) \\ R_{3z}(-1) & R_{3z}(0) & \cdots & R_{3z}(O_z-1) \\ \vdots & \vdots & \vdots & \vdots \\ R_{3z}(-O_z) & R_{3z}(-O_z+1) & \cdots & R_{3z}(0) \end{pmatrix} \begin{pmatrix} 1 \\ b_{1z} \\ \vdots \\ b_{O_z z} \end{pmatrix} = \begin{pmatrix} \beta_z \\ 0 \\ \vdots \\ 0 \end{pmatrix}$$

$z = X, Y$ where the skewness ($\beta_z$) and the coefficients ($b_{1z}, \ldots, b_{O_z z}$), $z = X, Y$, can be obtained by solving the linear system of equations.

The average auto/cross complex triple product of $X_i(t)$ and $Y_i(t)$ are computed in step 918 as the cubic root of the triple product of the skewnesses, $(\beta_X \beta_Y \beta_Y)^{1/3}$, divided by the triple product of the Fourier transforms of the AR filter coefficients ($H_z(f)$), i.e., $BC(f_1, f_2) = (\beta_X \beta_Y \beta_Y)^{1/3} / (H_X(f_1) H_Y(f_2) H_Y^*(f_1+f_2))$ $$H_z(f) = 1 + \sum_{i=1}^{O_z} b_{iz} e^{-j2\pi f i}$$

$z = X, Y$ and $BR(f_1, f_2)$ is the average auto/cross real triple product:

$BR(f_1, f_2) = P_X(f_1) P_Y(f_2) P_Y(f_1+f_2)$

After obtaining the average auto/cross complex and real triple products, the system computes the bispectral density, biphase, and bicoherence arrays in step 920 the same way as in steps 816, 818, 820. In step 922, the system returns the requested bispectral arrays to the Data Computation Unit 30.

Calculation of an Index of Neurostimulation Efficacy

An index may be constructed using features calculated from the spectral arrays as well as by means of other frequency and time domain methods. In the preferred embodiment, such an index is designed to quantify EEG changes related to neurostimulator treatment efficacy. Development of such an index requires a data set of EEG data from individuals with the specified pathological condition the neurostimulator is intended to treat, along with the neurostimulator status before and during the recording and an independent measure of treatment status and efficacy.

In the development of the present embodiment, EEG data was recorded from a series of patients with major depressive disorder (MDD) or obsessive-compulsive disorder (OCD) with implanted DBS stimulators. EEG recordings were made while patients were awake with their eyes closed. EEG data was recorded from electrode pairs $A_1$-$Fp_Z$ (left hemisphere) and $A_2$-$Fp_Z$ (right hemisphere) prior to DBS stimulation (the baseline recording) and subsequently during multiple on-off stimulator cycles. At the time of each recording, the subjects self-reported their mood on a scale from 1-10 (i.e., 1 and 10 being the worst and best moods imaginable) as well as their level of anxiety (1 being not anxious at all, 10 being the most anxious imaginable). The mood and anxiety scores are measures of patient status that are independent of the EEG, and the change in mood with treatment (here, neurostimulation) is an independent measure of treatment efficacy. To increase the dynamic range of the mood assessments, EEGs were recorded with the stimulator both off (typically resulting in poorer mood) and on (typically resulting in improved mood). For each of the channels $A_1$-$Fp_Z$ and $A_2$-$Fp_Z$, the various spectral arrays were calculated as described above, a separate array being calculated for the time period immediately preceding each of the patient's assessments of mood and anxiety. Average EEG spectral arrays were calculated for all frequencies at 0.5 Hz resolution using 2-sec records of the first 30 seconds of artifact-free EEG.

In the preferred embodiment, a feature was constructed as the absolute power within the alpha frequency range (8-12 Hz) averaged over 2 EEG channels (A1-Fpz and A2-Fpz). This feature, the Absolute Alpha Power, is calculated as $$\text{Absolute\_Alpha\_Power} = \frac{\left( \sum_{f=8}^{12} P(f)_{A1\_FPz} + \sum_{f=8}^{12} P(f)_{A2\_FPz} \right)}{2}$$

The absolute power is summed in the alpha frequency region separately for each EEG channel, and the average alpha power is calculated over the 2 channels. The correlation of Absolute Alpha Power with mood score is systematically negative, so that alpha power decreases as subjects' mood scores increase. The Pearson linear correlation between absolute alpha power and mood score is statistically significant ($R=-0.821$, $p=0.012$).

Although the preferred embodiment uses two channels of EEG data, alternate embodiments may include data from one or a plurality of channels. In addition, biological systems vary to some degree, so somewhat different frequency ranges are likely to provide equivalent performance. Similarly, other frequency ranges may be used.

Another feature calculated from the power spectral array in the preferred embodiment is the difference in absolute power in the alpha frequency range (8 Hz$\leq$f$\leq$12 Hz) between the left and right hemispheres. This feature, the Absolute Alpha Asymmetry, or interhemispheric difference, is calculated as $$\text{Absolute\_Alpha\_Asymmetry} = \sum_{f=8}^{12} P(f)_{A1\_FPz} - \sum_{f=8}^{12} P(f)_{A2\_FPz}$$

Upon analysis, it was determined that patients' Absolute Alpha Asymmetry was correlated with mood score. Another means to calculate a bilateral difference is a relative power asymmetry. Dividing the absolute alpha powers of the left and right channels by their respective total powers over the range of frequencies of interest (in this case, 0.5-20 Hz) normalizes the data for changes in overall EEG power levels and increases the correlation with mood score. The normalized alpha power of each channel is called the Relative Alpha Power and the difference in the left and right Relative Alpha Powers is the Relative Alpha Asymmetry. This parameter is calculated as the relative alpha power of the left hemisphere (i.e., calculated from EEG channel $A_1$-$Fp_Z$) minus the relative alpha power of the right hemisphere (i.e., calculated from EEG channel $A_2$-$Fp_Z$).

$$\text{Relative\_Alpha\_Asymmetry} = \left( \frac{\sum_{f=8}^{12} P(f)_{A1\_FPz}}{\sum_{f=0.5}^{20} P(f)_{A1\_FPz}} \right) - \left( \frac{\sum_{f=8}^{12} P(f)_{A2\_FPz}}{\sum_{f=0.5}^{20} P(f)_{A2\_FPz}} \right)$$

The correlation of the inter-hemispheric difference in Relative Alpha Power with mood score is systematically positive, so that Relative Alpha Power of the left side of the head increases relative to the Relative Alpha Power on the right side of the head as subjects feel better. The Pearson linear correlation (R) between Relative Alpha Asymmetry and the corresponding mood score in MDD is 0.838 ($p<0.001$). In the combined population of MDD and OCD patients, the correlation of change in Relative Alpha Asymmetry with mood score is $R=0.766$ and is independent of disease etiology. A further finding is that the change in Relative Alpha Asymmetry is inversely correlated with the change in Anxiety Score over the same period ($R=-0.605$, $p<0.02$); this relationship is also consistent across individuals and etiologies (MDD and OCD). Again, although the preferred embodiment uses two channels of EEG data, alternate embodiments may include data from one or a plurality of channels. In addition, biological systems vary to some degree, so somewhat different frequency ranges are likely to provide equivalent performance. Similarly, other frequency ranges may be used.

An index is often specified to have the form of a linear equation. Those skilled in the art will readily recognize that other forms, such as non-linear equations or neural networks, may be used as well. In the preferred embodiment, the index has the general form $$\text{Index} = c_0 + \sum_{i=1}^{p} c_i F_i$$

where $c_0$ is a constant, $\{F_i, i=1,2,\ldots,p\}$ are a set of features, $\{c_i, i=1,2,\ldots,p\}$ are a set coefficients corresponding to the features and p is the number of features.

An index to track the efficacy of neurostimulation to effect mood changes may be calculated as:

$$Index_{Mood\_1} = c_0 + c_1 F_1$$

$$c_0 = \frac{100 \max(F_1)}{(\max(F_1) - \min(F_1))} = \frac{100}{\left(1 - \frac{\min(F_1)}{\max(F_1)}\right)}$$

$$c_1 = \frac{100 - c_0}{\min(F_1)} = \frac{-100}{(\max(F_1) - \min(F_1))}$$

$$F_1 = Absolute\_Alpha\_Power$$

Here, $c_0$ and $c_1$ are defined such that the range of $Index_{Mood\_1}$ will be between 0 (least efficacious state) and 100 (most efficacious state) for a feature $F_1$ (e.g., absolute alpha power) that decreases as efficacy increases (negative correlation). Based upon the database used to derive this example, $\min(F_1)=122.9$ and $\max(F_1)=191.9$, resulting in $c_0=278.12$ and $c_1=-1.45$. The high correlation of alpha power with mood score (R=−0.821, p=0.012) indicates that $Index_{Mood\_1}$ is a sensitive measure of mood state.

Another index which quantifies the efficacy of neurostimulation to effect mood changes may be calculated using the Relative Alpha Asymmetry as:

$$Index_{Mood\_2} = c_0 + c_1 F_1$$

$$c_0 = \frac{-100 \min(F_1)}{(\max(F_1) - \min(F_1))} = \frac{100}{\left(1 - \frac{\max(F_1)}{\min(F_1)}\right)}$$

$$c_1 = \frac{100 - c_0}{\min(F_1)} = \frac{100}{(\max(F_1) - \min(F_1))}$$

$$F_1 = Relative\_Alpha\_Asymmetry$$

Again, $c_0$ and $c_1$ are defined such that the range of $Index_{Mood\_2}$ will be between 0 (least efficacious state) and 100 (most efficacious state) for feature $F_1$ (e.g., Relative Alpha Asymmetry) that increases as efficacy increases (positive correlation). In the data set used to derive these results, $\min(F_1)=-0.048$ and $\max(F_1)=0.068$, resulting in $C_0=41.379$ and $c_1=862.069$. The high correlation of inter-hemispheric difference in relative alpha power with mood score indicates that $Index_{Mood\_2}$ is a sensitive measure of mood state. Note that the different form of the constants c0 and c1 in the two embodiments is due to the sign of the correlation (positive vs. negative) between $F_1$ and mood score. It should be noted that in the case of a single feature, the values of $c_0$ and $c_1$ are simply scaling factors; if $c_0=0$ and $c_1=1$, the value of the index consisting of a single feature is simply the value of feature itself. Indices comprising a plurality of features may be implemented as well, using the same general form as in the equations above. Although the preceding discussion is specific to indices derived from inter-hemispheric EEG channels, features may calculated from one or a plurality of unilateral EEG channels as well as other montages of bilateral EEG channels. Indices may also be constructed of both unilateral and bilateral features in combination.

Features computed from different frequency bands may also be used. For example, in a preliminary development effort, it was determined that the relative power in the theta band (4-8 Hz) calculated from either hemisphere was negatively correlated with patients' mood scores. Therefore, an alternate index of mood score may be computed using $F_1$=relative theta power, $\min(F_1)=0.005$ and $\max(F_1)=0.310$, yielding $$Index_{Mood\_3} = c_0 + c_1 F_1$$

$$c_0 = \frac{100}{\left(1 - \frac{\min(F_1)}{\max(F_1)}\right)} = 101.639$$

$$c_1 = \frac{100 - c_0}{\min(F_1)} = -327.800$$

$$F_1 = Relative\_Theta\_Power = \frac{\sum_{f=4}^{8} P(f)_{A1\_FPz}}{\sum_{f=0.5}^{20} P(f)_{A1\_FPz}}$$

Although this discussion is specific to indices derived from the power spectral array, it is not limited to this method. Features may be calculated from various frequency regions of bispectral arrays (i.e., bispectrum, complex triple product, real triple product, biphase and bicoherence, all for both auto and cross formulations), as well as cross spectral and coherence arrays. Other methods may be used to derive features, such as medians, standard deviations and variances, percentiles, absolute power within a region bounded by specified frequencies, relative power (absolute power as a percentage of total power within a region bounded by specified frequencies), neural networks, fractal spectral analysis, measures derived from information theory such as entropy and complexity, and other statistical measures known to those skilled in the art. Features may also be derived from various methods of time domain analysis such as pattern or template matching. Features may also quantify the presence or absence of a specific condition over a time period, or the degree to which a specific condition is met over a specific time period (e.g., the percent of time in a recent period that the power in a specific frequency band of a power or bispectral array was less than a threshold value). Detectors of specific conditions or signal types may also be used as features or as an index having just two or more discrete states.

The computed indices or features are reflective of a patient's neurological or psychological state. In the described embodiments, the various $Index_{Mood\_i}$ (i=1,2,3) are measures of the patient's mood, as quantified by the mood score. The invention may therefore be used to optimize a specific treatment modality by varying the treatment parameters such that $Index_{Mood\_i}$ is increased to a maximum value. In the case of neurostimulation, the treatment parameters include the amplitude, frequency, polarity and pulse width of the stimulating signal, as well as the subset of selected stimulating electrodes. For other treatment modalities, the treatment parameters may include dosage (pharmacological treatment), stimulation voltage (ECT) and field strength (TMS).

The system and method of the present invention monitors the treatment efficacy of neurostimulation. Because the invention monitors the change in neural activity resulting from treatment, it is not dependent on a specific treatment modality. Therefore, the invention may be used to monitor the efficacy of other types of treatment as well, including but not restricted to pharmacological treatment, electroconvulsive therapy and transcranial magnetic stimulation.

Testing Methodologies to Improve Sensitivity and Specificity

The sensitivity and specificity of the invention may be increased through the use of differential testing methodologies. Differential test methodologies use 2 or more consecutive assessments, and analyze the change in the value of the test metric between the assessments as well as the actual values at each of the assessments. The assessments are generally conducted under different conditions, such as sleep or under the influence of a stressor such as a mental task; these are compared to a baseline assessment. Patients with dementia, depression, OCD and other neurological disorders exhibit EEG responses different from that of normal subjects in a differential testing methodology. This description will describe several differential testing methodologies which may be used to increase the performance of the derived indices. Preferably, the test metric is an index derived from the EEG spectral arrays, as well as other parameters, and will be denoted here as INDEX.

One differential test methodology takes advantage of the patient's varying response when the stimulator is on and when it is off. The electrodes are first applied to the subject, who is instructed to sit quietly with eyes either open or closed. A baseline assessment is performed with the neurostimulator 60 off in which the DAU 20 acquires a segment of EEG and transmits it to the DCU 30 for analysis. Generally, segments of several minutes are used to calculate the INDEX values. A first value of INDEX (denoted as $INDEX_{stim\_off}$) is calculated by the DCU 30 from the EEG segment. The neurostimulator 60 is then turned on and a second segment of EEG is acquired by the DAU 20 and transmitted to the DCU 30 for analysis. A second value of INDEX (denoted as $INDEX_{stim\_on}$) is calculated by the DCU 30 from EEG acquired during the second assessment period. This later assessment period may be when the neurostimulator 60 is turned on, or when it is turned off after having been on for a period of time. Examining the acquired data for artifact and either removing the detected artifact or excluding the artifacted portion of the acquired data from analysis is an integral part of calculating an INDEX value. The difference between the INDEX values obtained at these two assessment times, $INDEX_{stim\_on}-INDEX_{stim\_off}$, constitutes an Index which may be used to quantify treatment efficacy. For example, the correlation between Relative Alpha Asymmetry and mood score may be improved by comparing the change in Relative Alpha Asymmetry from baseline (stimulator off) to subsequent periods when the stimulator was either on or was off after having been on. The change in Relative Alpha Asymmetry in MDD is strongly correlated with the change in mood score over the same period ($R=0.872$, $p<0.001$). This relationship is independent of stimulation mode (bipolar stimulation, monopolar stimulation, and stimulator off). This differential methodology could be expanded by comparing INDEX values with the neurostimulator at different control settings, e.g., different stimulation signal frequencies (repetition rates), pulse widths, pulse amplitudes and duty cycles, lead selections, and stimulator signal polarities.

Another test methodology calculates the difference between a first value of INDEX calculated from EEG acquired with the subject's eyes open and a second value of INDEX calculated from EEG acquired with the subject's eyes closed. The neurostimulator 60 may be either on or off during any of the assessments. The electrodes 15 are first applied to the subject, who is instructed to sit quietly with eyes open. A segment of EEG is acquired by the DAU 20 and transmitted to the DCU 30 for analysis. Generally, segments of several minutes are used to calculate the INDEX values. The subject is next directed to sit quietly with eyes closed, and a second segment of EEG is acquired by the DAU 20 and transmitted to the DCU 30 for analysis. The DCU 30 calculates INDEX values for both the first and second periods of acquired data, referred to as $INDEX_{eyes\_open}$ and $INDEX_{eyes\_closed}$. Examining the acquired data for artifact and either removing the detected artifact or excluding the artifacted portion of the acquired data from analysis is an integral part of calculating an INDEX value. The numerical difference between $INDEX_{eyes\_open}$ and $INDEX_{eyes\_closed}$ constitutes an Index which may be used to quantify treatment efficacy.

A third differential test methodology calculates the difference between a first value of INDEX calculated from EEG acquired with the subject in a relaxed state and a second value of INDEX calculated from EEG acquired while the subject is performing a mental calculation task. The neurostimulator 60 may be either on or off during any of the assessments. The subject may be directed to keep his/her eyes open during both recording periods. Alternatively, the subject may be directed to close their eyes during both recording periods, though this may restrict the mental calculation tasks that may be chosen. The mental calculation task may be any simple task or set of tasks chosen to provide adequate difficulty yet universal enough to not require special training or a level of education not universal in the population to be tested. Two example tasks are mental addition and subtraction of numbers, as would be required in balancing a check book or counting backward from one hundred by threes, and the calculation of the number of days between two dates. The electrodes 15 are first applied to the subject, who is instructed to sit quietly. A segment of EEG is acquired by the DAU 20 and transmitted to the DCU 30 for analysis. Again, segments of several minutes are used to calculate the INDEX values. The subject is next given instruction in the mental task and then asked to complete it. A second segment of EEG is acquired by the DAU 20 during the period of mental calculation. The acquired data is then transmitted to the DCU 30 for analysis. The DCU 30 calculates INDEX values for both the first and second periods of acquired data, referred to as $INDEX_{baseline}$ and $INDEX_{task}$. The numerical difference between $INDEX_{task}$ and $INDEX_{baseline}$ constitutes an Index which may be used to quantify treatment efficacy.

Automated Adjustment of Neurostimulator Parameters to Obtain Maximal Treatment Efficacy A baseline measure of EEG state can be assessed by calculation of the Index when the neurostimulator is disabled. This value may be compared to the Index calculated at various neurostimulator parameters (settings). The greatest treatment efficacy and therefore the optimal neurostimulator parameters would correspond to those which maximized the difference between the corresponding Index values and the baseline Index value. As the Index value is a univariate measure of neurostimulator efficacy, a control signal can be supplied from the DCU 30 to the neurostimulator 60. This control signal could be used to control the various neurostimulator parameters. Various combinations of neurostimulator settings could be automatically selected by the DCU 30 and an Index value calculated for each setting. The optimal neurostimulator parameters would be determined to be those at which the Index is the greatest difference from a baseline (neurostimulator off) value of the Index. The DCU 30 would then command the neurostimulator to configure itself using the parameters determined to be optimum.

In general, neurostimulators have 4 or more parameters that may be adjusted, often in a continuous fashion. Therefore, the number of parameter combinations is very large.

Different strategies may be employed to reduce the number of parameter combinations examined while still finding a local maximum value of the index (assuming that maximum treatment efficacy is obtained with a maximal INDEX value). For instance, all parameters may be initially set at a nominal value, then one parameter is adjusted over its range. The DCU 30 will record the parameter value that generates the maximum INDEX difference from baseline. This process will be repeated for all parameters. At the end of the process, the neurostimulator 60 will be configured by the DCU 30 setting each parameter to the optimum setting. In an alternate embodiment of the index, settings that produce local minimum value of the index may be desired. The invention described here uses neurostimulation as a treatment. However, the same invention may be applied to other treatments, such as administration of pharmacological agents, electroconvulsive therapy and transcranial magnetic stimulation. In the case of the former, the agent, the dose or the dosing regimen may be varied; in the latter two, the parameters of the shock may be varied.

While the foregoing invention has been described with reference to its preferred embodiments, various alterations and modifications will occur to those skilled in the art. All such alterations and modifications are intended to fall within the scope of the appended claims.

What is claimed is:

1. A system for assessing the efficacy of treatment of a neurological disorder comprising:
   at least two electrodes for acquiring electrophysiological signals from the body suffering from a neurological disorder which is one or more of depression, major depressive disorder, obsessive compulsive disorder, dementia, mood disorders and anxiety disorders, wherein one of said at least two electrodes for acquiring electrophysiological signals from the body is positioned at electrode position $Fp_z$;
   a processor for calculating from said electrophysiological signals at least one feature relating to the efficacy of said treatment without referencing said at least one feature to a normative data set, said at least one feature being a measure of a self-reported mood or anxiety score.

2. The system for assessing the efficacy of treatment of a neurological disorder of claim 1 wherein said treatment is neurostimulation.

3. The system for assessing the efficacy of treatment of a neurological disorder of claim 2 wherein said neurostimulation is deep brain stimulation.

4. The system for assessing the efficacy of treatment of a neurological disorder of claim 2 wherein said neurostimulation is vagus nerve stimulation.

5. The system for assessing the efficacy of treatment of a neurological disorder of claim 1 wherein said treatment is the administration of a pharmacological agent.

6. The system for assessing the efficacy of treatment of a neurological disorder of claim 1 wherein said treatment is electroconvulsive therapy.

7. The system for assessing the efficacy of treatment of a neurological disorder of claim 1 wherein said treatment is transcranial magnetic stimulation.

8. The system for assessing the efficacy of treatment of a neurological disorder of claim 1 wherein said processor calculates at least two features and combines said at least two features into an index.

9. The system for assessing the efficacy of treatment of a neurological disorder of claim 1 wherein said processor calculates at least one feature from a spectral array.

10. The system for assessing the efficacy of treatment of a neurological disorder of claim 8 wherein said processor calculates at least one feature from a power spectral array.

11. The system for assessing the efficacy of treatment of a neurological disorder of claim 8 wherein said processor calculates at least one feature from a bispectral array.

12. The system for assessing the efficacy of treatment of a neurological disorder of claim 1 wherein said at least one feature is a time domain feature.

13. The system for assessing the efficacy of treatment of a neurological disorder of claim 1 wherein said at least two electrodes are placed in a bilateral montage.

14. The system for assessing the efficacy of treatment of a neurological disorder of claim 1 wherein said at least two electrodes are placed in an unilateral montage.

15. The system for assessing the efficacy of treatment of a neurological disorder of claim 1 wherein said feature is the interhemispheric difference in a metric calculated from each electrophysiological signal.

16. The system for assessing the efficacy of treatment of a neurological disorder of claim 15 wherein said metric is a spectral feature.

17. The system for assessing the efficacy of treatment of a neurological disorder of claim 15 wherein said metric is a time domain feature.

18. A system for assessing the efficacy of treatment of a neurological disorder comprising:
   at least two electrodes for acquiring electrophysiological signals from a body suffering from a neurological disorder which is one or more of depression, major depressive disorder, obsessive compulsive disorder, dementia, mood disorders and anxiety disorders, wherein one of said at least two electrodes for acquiring electrophysiological signals from the body is positioned at electrode position $Fp_z$;
   data acquisition circuitry for acquiring from said electrodes a first electrophysiological signal representing a baseline condition and a second electrophysiological signal representing a subsequent condition;
   a processor for calculating from said electrophysiological signals received from the data acquisition circuitry:
   (a) at least one feature relating to the patient state during the baseline condition, without referencing said at least one feature relating to the patient state during the baseline condition to a normative data set, said at least one feature relating to the patient state during the baseline condition being a measure of a self-reported mood or anxiety score;
   (b) at least one feature relating to the patient state during the subsequent condition, without referencing said at least one feature relating to the patient state during the subsequent condition to a normative data set, said at least one feature relating to the patient state during the subsequent condition being a measure of a self-reported mood or anxiety score; and
   (c) the difference between said features relating to the baseline and subsequent conditions, such that said difference relates to the efficacy of said treatment.

19. A system for optimizing the efficacy of treatment of a neurological disorder comprising:
   at least two electrodes for acquiring electrophysiological signals from a body suffering from a neurological disorder which is one or more of depression, major depressive disorder, obsessive compulsive disorder, dementia, mood disorders and anxiety disorders, wherein one of said at least two electrodes for acquiring electrophysiological signals from the body is positioned at electrode position $Fp_z$;

processor for calculating from said electrophysiological signals at least one feature relating to the efficacy of said treatment without referencing said at least one feature to a normative data set, said feature being a measure of a self-reported mood or anxiety score;

data acquisition circuitry for acquiring said electrophysiological signals from said electrodes and converting said electrophysiological signals to a form usable by said processor;

a processor for varying the treatment parameters of a neurostimulator in order to maximize the calculated treatment efficacy.

20. A method of assessing the efficacy of treatment of a neurological disorder comprising the steps of:

acquiring electrophysiological signals from a body suffering from a neurological disorder which is one or more of depression, major depressive disorder, obsessive compulsive disorder, dementia, mood disorders and anxiety disorders, said signals being acquired through electrodes placed on the body, wherein one of said at least two electrodes for acquiring electrophysiological signals from the body is positioned at electrode position $Fp_z$;

calculating from said electrophysiological signals at least one feature relating to the efficacy of said treatment without referencing said at least one feature to a normative data set, said feature being a measure of a self-reported mood or anxiety score.

21. The method of assessing the efficacy of treatment of a neurological disorder of claim 20 wherein said treatment is neurostimulation.

22. The method of assessing the efficacy of treatment of a neurological disorder of claim 21 wherein said neurostimulation is deep brain stimulation.

23. The method of assessing the efficacy of treatment of a neurological disorder of claim 21 wherein said neurostimulation is vagus nerve stimulation.

24. The method of assessing the efficacy of treatment of a neurological disorder of claim 20 wherein said treatment is the administration of a pharmacological agent.

25. The method of assessing the efficacy of treatment of a neurological disorder of claim 20 wherein said treatment is electroconvulsive therapy.

26. The method of assessing the efficacy of treatment of a neurological disorder of claim 20 wherein said treatment is transcranial magnetic stimulation.

27. The method of assessing the efficacy of treatment of a neurological disorder of claim 20 further comprising the step of combining said features into an index.

28. The method of assessing the efficacy of treatment of a neurological disorder of claim 20 wherein said at least one feature is calculated from a spectral array.

29. The method of assessing the efficacy of treatment of a neurological disorder of claim 27 wherein said at least one feature is calculated from a power spectral array.

30. The method of assessing the efficacy of treatment of a neurological disorder of claim 27 wherein said at least one feature is calculated from a bispectral array.

31. The method of assessing the efficacy of treatment of a neurological disorder of claim 20 wherein said at least one feature is a time domain feature.

32. The method of assessing the efficacy of treatment of a neurological disorder of claim 20 wherein said at least two electrodes are placed in a bilateral montage.

33. The method of assessing the efficacy of treatment of a neurological disorder of claim 20 wherein said at least two electrodes are placed in an unilateral montage.

34. The method of assessing the efficacy of treatment of a neurological disorder of claim 20 wherein said feature is the interhemispheric difference in a metric calculated from each electrophysiological signal.

35. The method of assessing the efficacy of treatment of a neurological disorder of claim 34 wherein said metric is a spectral feature.

36. The method of assessing the efficacy of treatment of a neurological disorder of claim 34 wherein said metric is a time domain feature.

37. A method of assessing the efficacy of treatment of a neurological disorder comprising:

positioning a least two electrodes on a body being treated for a neurological disorder which is one or more of depression, major depressive disorder, obsessive compulsive disorder, dementia, mood disorders and anxiety disorders, wherein one of said at least two electrodes for acquiring electrophysiological signals from the body is positioned at electrode position $Fp_z$;

acquiring a first electrophysiological signal from the body at a baseline condition;

acquiring a second electrophysiological signal from the body during a subsequent condition;

calculating at least one feature relating to the patient state during the baseline condition without referencing said at least one feature relating to the patient state during the baseline condition to a normative data set, said at least one feature relating to the patient state during the baseline condition being a measure of a self-reported mood or anxiety score;

calculating at least one feature relating to the patient state during the subsequent condition without referencing said at least one feature relating to the patient state during the subsequent condition to a normative data set, said at least one feature relating to the patient state during the subsequent condition being a measure of a self-reported mood or anxiety score;

calculating at the difference between the features calculated during the baseline and subsequent conditions, such that the difference relates to the efficacy of said treatment.

38. A method of optimizing the efficacy of treatment of a neurological disorder comprising:

positioning at least two electrodes on a body being treated for a neurological disorder which is one or more of depression, major depressive disorder, obsessive compulsive disorder, dementia, mood disorders and anxiety disorders, wherein one of said at least two electrodes for acquiring electrophysiological signals from the body is positioned at electrode position $Fp_z$;

acquiring electrophysiological signals from the body;

calculating at least one feature relating to the efficacy of said treatment without referencing said at least one feature to a normative data set, said at least one feature being a measure of a self-reported mood or anxiety score;

varying treatment parameters in order to maximize the calculated treatment efficacy.

* * * * *